(12) United States Patent
Moore et al.

(10) Patent No.: US 7,092,843 B2
(45) Date of Patent: Aug. 15, 2006

(54) APPARATUS AND METHOD FOR SUPPRESSING INSIGNIFICANT VARIATIONS IN MEASURED SAMPLE COMPOSITION DATA, INCLUDING DATA MEASURED FROM DYNAMICALLY CHANGING SAMPLES USING X-RAY ANALYSIS TECHNIQUES

(75) Inventors: Michael D. Moore, Alplaus, NY (US); John H. Burdett, Jr., Charlton, NY (US); Ian Radley, Glenmont, NY (US); Stuart M. Shakshober, Hudson, NY (US)

(73) Assignee: X-Ray Optical Systems, Inc., East Greenbush, NY (US)

( * ) Notice: Subject to any disclaimer, the term of this patent is extended or adjusted under 35 U.S.C. 154(b) by 20 days.

(21) Appl. No.: 10/971,175

(22) Filed: Oct. 21, 2004

(65) Prior Publication Data

US 2005/0086275 A1    Apr. 21, 2005

Related U.S. Application Data

(60) Provisional application No. 60/513,112, filed on Oct. 21, 2003.

(51) Int. Cl.
*G06F 15/00* (2006.01)
*G06F 17/18* (2006.01)
*G06F 19/00* (2006.01)
*G06F 11/30* (2006.01)

(52) U.S. Cl. .................................................... 702/179

(58) Field of Classification Search ................ 702/179
See application file for complete search history.

(56) References Cited

U.S. PATENT DOCUMENTS 5,838,561 A * 11/1998 Owen .......................... 700/32

* cited by examiner

*Primary Examiner*—John Barlow
*Assistant Examiner*—Sujoy Kundu
(74) *Attorney, Agent, or Firm*—Jeffrey R. Klembczyk, Esq.; Kevin P. Radigan, Esq.; Heslin Rothenberg Farley & Mesiti, P.C.

(57) ABSTRACT

A measurement and processing technique enabling x-ray analysis systems to handle dynamically changing samples and other conditions resulting in both significant and insignificant measurement changes. A stream of input values related to measured compositional information of the sample is received, and a stream of output compositional values is produced. The current output value $y[n]$ is set as a function of the received input value $x[n]$ if the received input value $x[n]$ differs from $x[n-1]$ by more than an intensity-dependent deviation limit; and alternatively the current output $y[n]$ is set as a function of the previous output $y[n-1]$ and the received input value $x[n]$ if the received input value $x[n]$ differs from $x[n-1]$ by less than the intensity-dependent deviation limit. The intensity-dependent deviation limit is maintained as a function of the intensity of the measured compositional information. Types of dynamically changing samples to which the technique is applicable include fluid streams and sheet production, monitored by, e.g., XRF and XRD systems.

27 Claims, 8 Drawing Sheets fig. 1 fig. 2 fig. 3 fig. 4 fig. 5 fig. 6 fig. 7A fig. 7B fig. 7C fig. 8 fig. 9

APPARATUS AND METHOD FOR SUPPRESSING INSIGNIFICANT VARIATIONS IN MEASURED SAMPLE COMPOSITION DATA, INCLUDING DATA MEASURED FROM DYNAMICALLY CHANGING SAMPLES USING X-RAY ANALYSIS TECHNIQUES

CROSS-REFERENCE TO RELATED APPLICATION

This application claims the benefit of U.S. Provisional Application No. 60/513,112, filed Oct. 21, 2003, which is hereby incorporated herein by reference in its entirety.

TECHNICAL FIELD

The present invention relates in general to analytical measurement systems. More particularly, the present invention relates to techniques for filtering insignificant measurement changes from a stream of measurement values in, for example, x-ray fluorescence and diffraction systems analyzing dynamically changing samples.

BACKGROUND OF THE INVENTION

X-ray analysis techniques have been some of the most significant developments in twentieth-century science and technology. The use of x-ray fluorescence, diffraction, spectroscopy, imaging, and other x-ray analysis techniques has led to a profound increase in knowledge in virtually all scientific fields.

Recent x-ray systems, occasioned in some instances by government regulations (i.e., monitoring the level of sulfur in fuel pipelines) or advanced production requirements (i.e., monitoring the texture of superconducting tapes under production) are confronted with the problems of samples moving past the detectors (referred to herein as dynamically changing samples) creating streams of unpredictably variant measurement data. This type of data stands in contrast to the relatively static data conventionally obtained by laboratory, bench-top x-ray analysis systems.

The expected measurement-to-measurement variance of data itself may change depending on the amplitude range of the measurements. Any measurement system should consider this when determining whether measurement changes are significant (warranting their reporting to the user as output values) or insignificant (warranting de-emphasis or deletion entirely).

What is required, therefore, are techniques, methods and systems which exploit some of the a-priori knowledge of x-ray measurement data, and effectively filter significant changes in measurements from insignificant changes.

SUMMARY OF THE INVENTION

To address the shortcomings of the prior art, and to enable x-ray analysis systems to handle dynamically changing samples and other conditions resulting in both significant and insignificant measurement changes, the present invention in one aspect is a technique (method, system and associated program code means) for suppressing statistically insignificant variations in data representing measured compositional information from a dynamically changing sample in an automated analysis system.

A stream of input values $x[n]$, $x[n-1]$, $x[n-2]$ ... related to measured compositional information of the sample is received, and a stream of output values $y[n]$, $y[n-1]$, $y[n-2]$, related to said compositional information, is produced. The current output value $y[n]$ is set as a function of the received input value $x[n]$ if the received input value $x[n]$ differs from $x[n-1]$ by more than an intensity-dependent deviation limit; and alternatively the current output $y[n]$ is set as a function of the previous output $y[n-1]$ and the received input value $x[n]$ if the received input value $x[n]$ differs from $x[n-1]$ by less than the intensity-dependent deviation limit. The intensity-dependent deviation limit is maintained as a function of the input values.

The intensity-dependent deviation limit is maintained as a function of:

$$\frac{|x[n] - x[n-1]|}{S\sqrt{x[n-1]}}$$

where S is a predetermined value controlling the deviation limit. The deviation limit can be clamped between 0 and 1 according to the following function:

$$p = 1 - \min\left(1, \max\left(\frac{|x[n] - x[n-1]|}{S\sqrt{x[n-1]}}, \delta\right)\right)$$

If p~a small (or 0) constant δ, then $x[n]$ differs from $x[n-1]$ by the deviation limit; and if p~1, then $x[n]$ differs from $x[n-1]$ by less than the deviation limit.

The value $y[n]$ is determined using a moving pole relationship as follows:

$$y[n] = (1-p)x[n] + py[n-1]$$

The technique is disclosed in combination with an x-ray engine measuring the compositional information using an x-ray analysis technique, the x-ray engine including a source for directing excitation x-ray, neutron, particle-beam or gamma ray radiation toward a sample, and a detector for detecting emissions emitted from the sample. The sample may be a fluid or solid, substantially moving relative to the source and/or detector (any form of relative movement included), and the x-ray engine may use an x-ray fluorescence or diffraction technique.

The deviation limit upon which the input values are tested is continuously updated as a function of the input values themselves. This adaptive maintenance of the deviation limit allows the x-ray engines to use the intrinsic properties of the Poisson distribution to advantage. This advantage is prior knowledge of the distribution of the random variables $x[n]$ and $x[n-1]$, as well as the increase in relative precision associated with the value of random variable $x[n]$ as the magnitude of $x[n]$ increases.

BRIEF DESCRIPTION OF THE DRAWINGS

The subject matter regarded as the invention is particularly pointed out and distinctly claimed in the claims at the conclusion of the specification. The foregoing and other objects, features, and advantages of the invention are apparent from the following detailed description taken in conjunction with the accompanying drawings in which:

DETAILED DESCRIPTION OF THE INVENTION

Generally stated, the present invention is directed to processing measurement data in a measurement system, for samples which are dynamically changing. Several such (x-ray fluorescence "XRF" and x-ray diffraction "XRD") measurement systems are first discussed, followed by a discussion of the present invention.

Focusing Excitation, Monchromatic Collection XRF:

Exemplary XRF systems are discussed in X-Ray Optical Systems, Inc. U.S. Provisional Application 60/299,371, filed Jun. 19, 2000, entitled "XRF SYSTEM INCLUDING FOCUSING OPTIC ON EXCITATION SIDE AND MONOCHROMATIC COLLECTION," and perfected as PCT Application PCT/US02/19272-WO02/103710, entitled "WAVELENGTH DISPERSIVE XRF SYSTEM USING FOCUSING OPTIC FOR EXCITATION AND A FOCUSING MONOCHROMATOR FOR COLLECTION," the entirety of which Applications are incorporated herein by reference.

Figure 1:
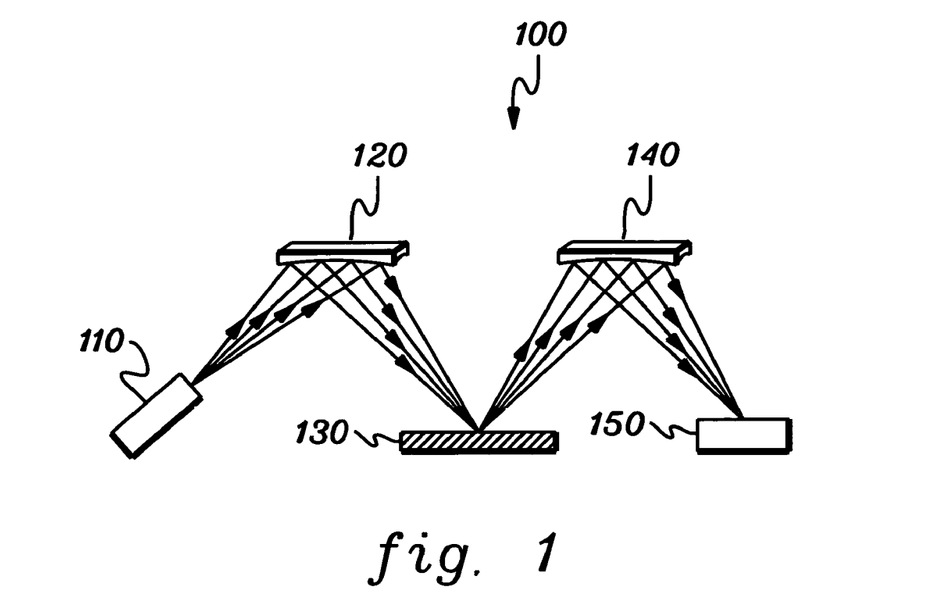
FIG. 1 depicts in schematic form one embodiment of an XRF engine 100 analyzing a sample.

As discussed in those Applications, FIG. 1 shows in schematic form, an exemplary XRF x-ray engine 100 including an x-ray source 110, a monochromatic optic 120, another monochromatic optic 140, and a detector 150 for analyzing sample 130.

X-ray source 110 is a source of x-ray radiation, such as an x-ray tube, a sealed source of radioactive material, or a source of electrons that impinge upon a metal surface and elicit the emission of x-ray radiation.

Monochromatic optic 120 is an optical element on the excitation side of XRF system 100 serving to transmit only radiation within a small range of energy to sample 130, e.g., with a range of energies between tens of electron-Volts, as opposed to polychromatic optics, which transmit radiation with energies ranging between thousands of electron-Volts. Monochromatic optic 140 is another monochromating optical element located on the collection side of XRF system 100 between sample 130 and detector 150. An example of monochromatic optics that are well suited to serve the purpose of monochromatic optic 120 and monochromatic optic 140 are doubly curved crystals, crystals with spherically or torroidally shaped crystal planes, which diffract only x-rays within an energy band of interest in accordance with Bragg's Law. Alternately, multilayer optics may serve the purpose of monochromatic optic 120 and monochromatic optic 140.

Detector 150 may be any x-ray detecting element, although XRF system 100 enables the inclusion of a detector 150 that does not need to have energy resolution capabilities, such as a simple counting detector like a gas-proportional counter or a scintillation counter.

Sample 130 is a material of which any type of compositional measurements are required. The term "compositional" when used herein includes the internal makeup of the sample, concentrations of any constituent thereof (desired or undesired), as well as any external characteristics, e.g., surface texture, phase, etc. As discussed elsewhere herein, the present invention is especially useful for such dynamically changing samples, i.e., samples which may be fluid flows (e.g., fuel) moving past the engine in refineries or pipelines, or solid sheets (i.e., steel or superconducting tapes) moving past the engine at some point in their fabrication.

An example of sample 130 may be a process flow such as diesel fuel from which a measurement of the concentration of sulfur is desired, or lubricating oil from which a measurement of the concentration of wear metal (iron) is desired. If sample 130 is a fluid flow, a window material may be included to enable the transmission of x-ray excitation radiation into an x-ray fluorescence out of sample 130.

In operation, XRF system 100 is well suited for applications such as compositional measurements in which the analyte is known and its presence and/or concentration is in question. Concentrations that may require sensitive measurements, e.g., in the parts per billion range, are well suited to XRF engine 100, as XRF engine 100 provides an absolute minimum of background noise when compared to conventional XRF systems. X-ray source 110 produces x-ray radiation. Monochromatic optic 120 collects the diverging photons and focuses them into a beam of monochromatic radiation onto sample 130. Monochromatic optic 120 is constructed to diffract photons only of an energy that is optimal for exciting and fluorescing the desired element contained within sample 130. Monochromating optic 120 absorbs photons of all other energies. The monochromatic focused beam impinges upon sample 130, exciting the analyte as well as anything else with a characteristic excitation energy lower than that of the incident beam. Sample 130 emits x-ray fluorescence photons that are unique to the elements within sample 130 of characteristic excitation energies equal to or less than the energy of the beam incident upon sample 130. Monochromatic optic 140 collects the emitted photons over a wide solid angle. Monochromatic optic 140 is constructed so as to diffract only fluorescence photons of the characteristic energy of the analyte in question and focuses these photons toward detector 150, which counts the number of photons incident upon it.

Monochromatically exciting sample 130 allows fluorescence of the analyte in question without the excitation of elements contained within sample 130 of a higher characteristic excitation energy, eliminating much of the scattering and unwanted background noise characterized by polychromatic excitation of samples used in conventional XRF systems. Further, monochromatic optic 120 collects x-ray radiation of the desired energy over a wide solid angle and focuses this energy into a high intensity beam onto sample 130. The focusing capability of monochromatic optic 120 eliminates the need for high energy x-ray sources, enabling desired incident energies onto sample 130 via a source 110 with a power requirement two orders of magnitude less than conventional means of attaining desired incident beam intensities.

Monochromatic optic 140 on the collection side of XRF system 100 collects fluorescence photons over a large solid angle, diffracts only the photons that are due to fluorescence of the analyte in question, and focuses them onto detector 150. Monochromatic optic 140 absorbs photons of all other energies. Knowledge of the desired analyte characteristic fluorescence energy allows monochromatic optic 140 to be designed so as to diffract only this particular energy to detector 150, effectively eliminating scatter and unwanted background noise and enabling the inclusion of a non-energy-sensitive detector 150. Detector 150 simply needs to count every photon that reaches detector 150 because each photon that reaches detector 150 is of the characteristic line desired. Detector 150 may therefore be a simple sealed gas proportional counter or a scintillation detector, resulting in an XRF system 100 having a much more compact size without the need to supply cooling to detector 150. Further, the wide collection angle of monochromatic optic 240 and its focusing capability results in a higher number of desired photons incident upon detector 150, increasing the achievable number of counts in a given time, and thereby enabling XRF system 100 to achieve desired sensitivities in shorter count times or to achieve more sensitive measurements in slightly longer count times.

Figure 2:
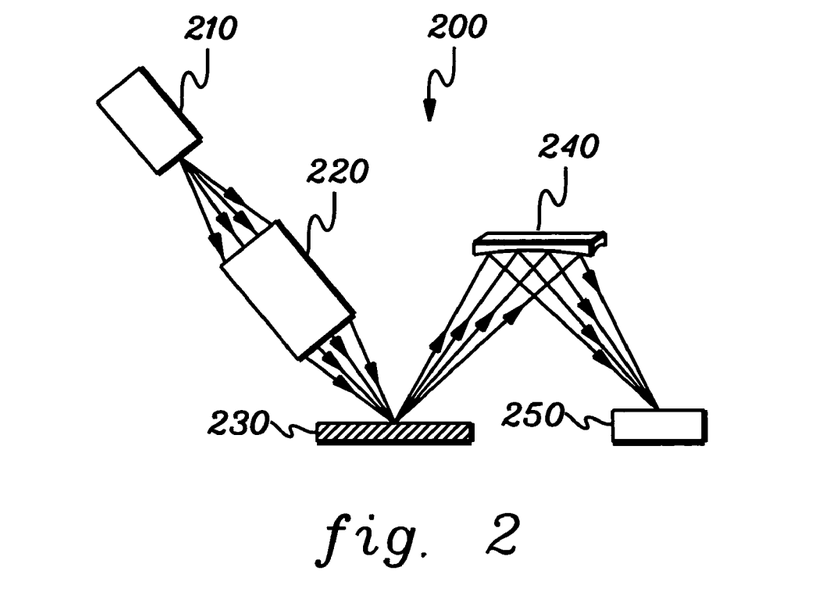
FIG. 2 depicts in schematic form another embodiment of an XRF engine 200 analyzing a sample.

FIG. 2 shows in schematic form an alternate embodiment of an XRF x-ray engine 200 that includes a source 210, a polychromatic optic 220, a monochromatic optic 240, and a detector 250 for analyzing a sample 230.

Polychromatic optic 220 is an optical element that transmits a broad range of photon energies while focusing and collimating the photons it collects. One example of a polychromatic optic that is well suited to serve the function of polychromatic optic 220 is a polycapillary optic, i.e., a bundle of thin, hollow tubes that transmit photons via total external reflection.

XRF engine 200 is well suited for applications in which analyte concentrations are higher than those in which XRF engine 100 may be applied, i.e., analyte concentrations on order of 0.5% as opposed to parts per billion, such that sensitivity is not as great a concern. Further, XRF engine 200 is well suited to efficient monitoring of several elements of dissimilar characteristic excitation energies contained in sample 230.

The optics discussed above (and below for XRD) used for controlling the excitation and/or emitted radiation can be of any suitable type, including monocapillary optics (see, e.g., X-Ray Optical Systems, Inc., U.S. Pat. No. 5,747,821, all of which is incorporated by reference herein in its entirety); polycapillary optics (see, e.g., X-Ray Optical Systems, Inc., U.S. Pat. Nos. 5,192,869; 5,175,755; 5,497,008; 5,745,547; 5,570,408; and 5,604,353;—all of which are incorporated by reference herein in their entirety); curved crystal optics (see e.g., X-Ray Optical, Inc., U.S. Pat. Nos. 6,285,506 and 6,317,483—all of which are incorporated by reference herein in their entirety); multi-layer optics and pin-hole or slot collimating optics. The optics may provide beam gain, as well as general beam control.

Also, as discussed above, monochromating optical elements may be desirable in the excitation and/or emission paths for narrowing the radiation bands depending on the sample material's characteristic signatures. Many of the optics discussed above, especially curved crystal optics and multi-layer optics, can be employed for this function, as set forth in many of the above-incorporated U.S. patents.

Optic/source combinations are also useable such as those disclosed in X-Ray Optical Systems, Inc., U.S. Provisional Application Ser. Nos. 60/398,968 (filed Jul. 26, 2002, entitled "METHOD AND DEVICE FOR COOLING AND ELECTRICALLY-INSULATING A HIGH-VOLTAGE, HEAT-GENERATING COMPONENT," and perfected as PCT Application PCT/US02/38803); 60/398,965 (filed Jul. 26, 2002, entitled "X-RAY SOURCE ASSEMBLY HAVING ENHANCED OUTPUT STABILITY," and perfected as PCT Application PCT/US02/38493); and 60/492,353 (filed Aug. 4, 2003, entitled "X-RAY SOURCE ASSEMBLY HAVING ENHANCED OUTPUT STABILITY USING TUBE POWER ADJUSTMENTS AND REMOTE CALIBRATION")—all of which are incorporated by reference herein in their entirety.

Figure 3:
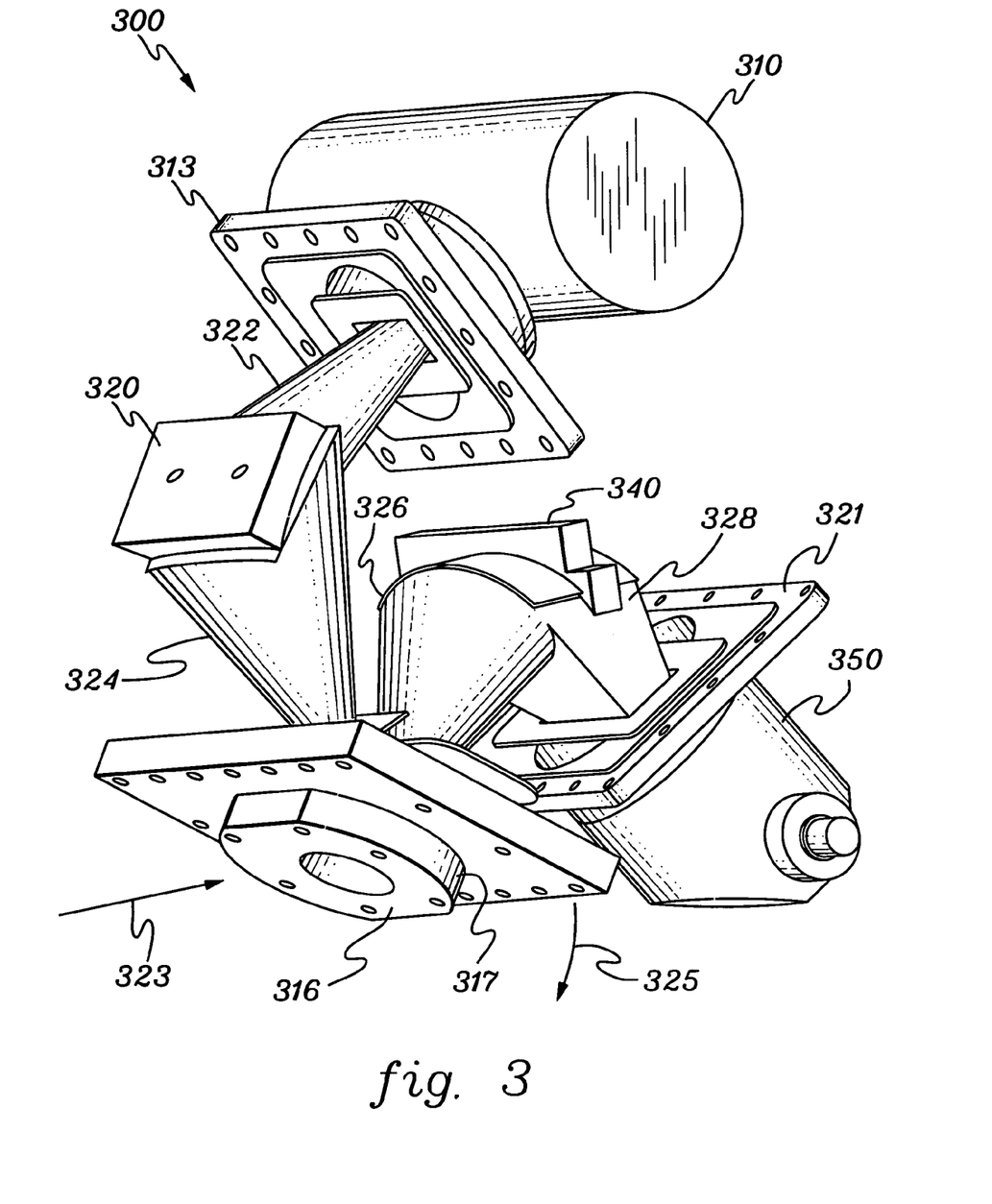
FIG. 3 depicts one exemplary embodiment of an x-ray engine implementing the principles of FIG. 1, optimized for analyzing a flowing fluid.

FIG. 3 depicts an exemplary embodiment of a fluid analysis, x-ray engine 300, based on components shown schematically in FIG. 1, and as discussed in further detail in X-Ray Optical Systems, Inc., U.S. Provisional Application Ser. No. 60/336,584 (filed Dec. 4, 2001, and entitled "X-RAY TUBE AND METHOD AND APPARATUS FOR ANALYZING FLUID STREAMS USING X-RAYS," perfected as PCT Application PCT/US02/38792-WO03/048745, entitled "X-RAY TUBE AND METHOD AND APPARATUS FOR ANALYZING FLUID STREAMS USING X-RAYS")—all of which are incorporated by reference herein in their entirety.

As discussed in those Applications, FIG. 3 shows exemplary spatial relationships between x-ray source assembly 310, sample excitation chamber assembly 316, x-ray detector assembly 350, and two x-ray focusing optics 320 and 340. Similar to the engine 100 shown schematically in FIG. 1, x-ray source assembly 310 produces an x-ray beam 322 which is focused by x-ray focusing and monochromating optic 320 to produce a focused monochromatic beam 324 on a fluid sample under test in excitation chamber assembly 316. The x-ray fluorescence created by the x-ray irradiation of the sample in sample excitation chamber assembly 316 generates x-ray fluorescent beam 326. Beam 326 is focused by x-ray focusing and monochromating optic 340 to provide a focused monochromatic x-ray beam 328 which is directed to x-ray detector assembly 350. Source assembly 310, holder assembly 316, and detector assembly 350 can include mounting flanges 313, 317, and 321, respectively, for mounting each assembly to a housing (not shown).

In one aspect, sample excitation chamber assembly 316 includes conduits 323 and 325 for introducing and removing, respectively, a sample from the sample excitation chamber, for example, continuous fluid (that is, gas or liquid) analysis. As discussed herein, the present invention is directed in large part to samples that dynamically change; here, a fluid flow past the excitation chamber assembly 316.

The fluid introduced to the conduit may be any type of liquid or gas that can be analyzed via x-ray fluorescence, but may be a fuel, for example, a fluid fuel, such as a petroleum-based fuel, for example, gasoline, diesel fuel, propane, methane, butane, or coal gas, among others. One constituent of petroleum-based fuels that can be detected via x-ray fluorescence is sulfur, though other constituents can also be detected. In one aspect, the fluid analyzed is diesel fuel in which the content of sulfur in the diesel fuel is characterized, for example, the concentration of the sulfur is determined. A system for characterizing the sulfur content in diesel fuel is marketed under the trademark SINDIE by X-Ray Optical Systems, Inc., of Albany, N.Y. When used for analyzing petroleum-based fuels, engine 300 can be used for sulfur analysis at the crude oil well, at the oil storage facilities, in fuel refineries, anywhere in the fuel distribution pipeline or network, or anywhere else where the sulfur content of a petroleum-based fuel is desired. The use of engine 300 eliminates the need for sample preparation and analytical reagents as is typically required in conventional methods of sulfur analysis of fuels. Engine 300 provides continuous, rapid, on-line fuel sulfur content so that a quality assessment and control can be effected as quickly as possible, but as discussed elsewhere herein, is required to address certain problems inherent in analyzing dynamically changing samples.

Figure 4:
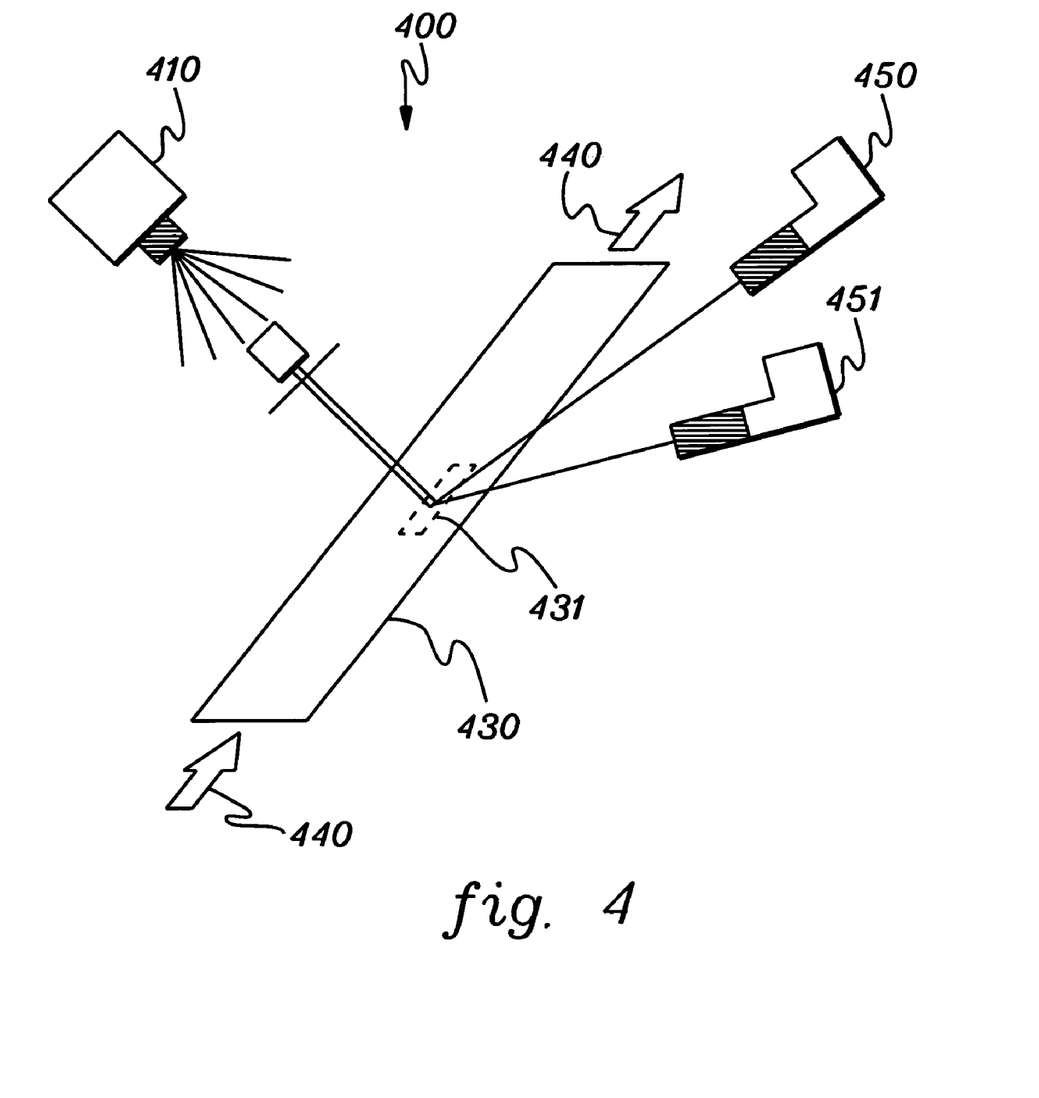
FIG. 4 depicts an in-situ, XRD system with fixed detectors monitoring the phase of a moving sample in a production setting.

Fixed Angle, In-Situ XRD Technique:

FIG. 4 depicts another x-ray engine 400 as disclosed in X-Ray Optical Systems, Inc., U.S. Provisional Application Ser. No. 60/492,400 (filed Aug. 4, 2003, entitled "FIXED ANGLE, IN-SITU X-RAY DIFFRACTION TECHNIQUE"), the entirety of which is incorporated herein by reference. This engine also analyzes a dynamically changing sample.

As discussed in that Application, x-ray diffraction engine 400 provides an in-situ system that enables, e.g., phase detection or monitoring and quantitative analysis of a sample area 431 of a moving sample 430. The x-ray diffraction engine 400 is particularly well suited for in-situ phase analysis of a moving sample (e.g., moving galvanized steel in a manufacturing environment subsequent to the application of a coating to the sample). The low power source 410 emits the diverging x-rays, which are collimated into a parallel beam by a collimating optic. This optic, and this source/optic assembly, may be a low-power source/optic combination as disclosed in the above-identified X-Ray Optical Systems, Inc. U.S. provisional and PCT patent applications. The parallel beam of x-rays impinges upon the sample area 431 and is diffracted by the crystalline phases in the sample according to Bragg's Law, and thereby generates the diffracted beams. The intensity of the x-rays within the diffracted beams is measured as a function of the diffraction angle. This diffraction pattern may be used in this example to identify and monitor the crystalline phases and other structural properties of the sample 430.

In the case where the diffraction angle of a specific phase is known, the diffraction pattern detection devices can be placed in fixed positions. As such, two detector assemblies 450 and 451, each with angular filters, may be included to acquire data from two different diffraction angles, respectively.

One detector may obtain "background" information from a region in which there is expected to be no diffraction peak, while the other detector measures the intensity of x-ray radiation directed to it from an angle in which the desired phase diffraction peak is expected to appear. A ratio is obtained by the signals input from the detectors to a controller and the amount of a given phase is determined. As the amount of the given phase increases, this ratio becomes greater than one, and an accurate determination of the percentage of that phase present in the sample 431 can be made.

FIG. 4 depicts an "in-line" version of an in-situ engine 400, coupled directly to a production line, and analyzing an area 431 of material 430 as it exists (possibly moving) in the production line, in a substantially predictable state (especially with respect to the theta, phi and chi angles discussed above). This type of environment may be applicable to a moving steel example, where steel sheets under production are moving along a movement path 440, or a superconductor texture measurement example, where superconductive tape is moving past the in-situ system. While the system may gather diffraction data through an area of the material, as a function of translation rate and sampling duration, the material could be stopped at discrete points with the measurement made at each point. However, continuous data sampling along an area of the material during continuous movement may be desirable for processing.

Figure 5:
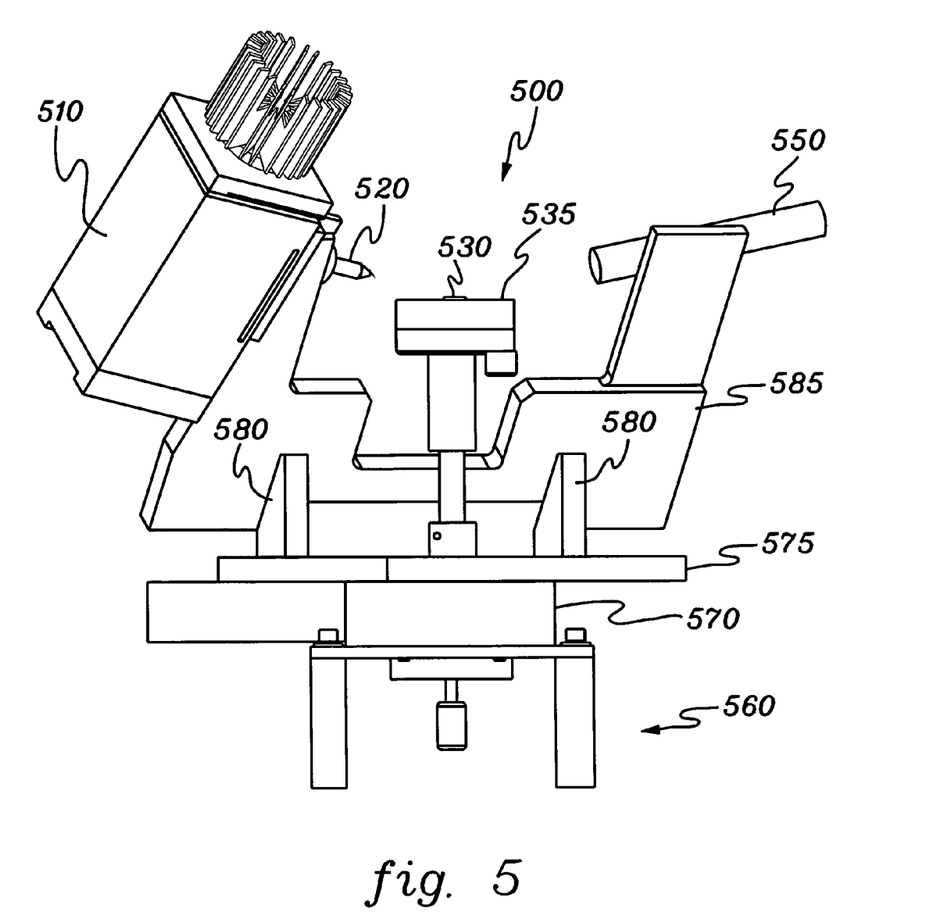
FIG. 5 shows a side, isometric view of an XRD system for monitoring the crystallographic texture of a reel-to-reel spool-fed continuous tape.

Aligned, Rotating Source/Detector XRD Technique:

FIG. 5 depicts another x-ray engine 500 as disclosed in X-Ray Optical Systems, Inc., U.S. Provisional Application Ser. No. 60/489,047 (filed Jul. 22, 2003, entitled "METHOD AND SYSTEM FOR X-RAY DIFFRACTION MEASUREMENTS USING AN ALIGNED SOURCE AND DETECTOR ROTATING AROUND A SAMPLE SURFACE"), the entirety of which is incorporated herein by reference.

FIG. 5 is a side, isometric view of this XRD engine. In this embodiment, the optic 520, and source 510/optic assembly may be a low-power source/optic combination as disclosed in the above-identified X-Ray Optical Systems, Inc. U.S. provisional and PCT patent applications. The source 510 is rigidly mounted to a rigid support structure, e.g., an approximately U-shaped plate 585 which traverses around and under the sample holder 535 (forming the tape 530's movement path). Here, the sample holder is fixedly mounted to a stationary post. The detector 550 is also rigidly mounted to the other end of plate 585. In one embodiment, the detector is a semiconductor, energy-sensitive detector with a detector area of about 25 $mm^2$. Plate 585 can be fixedly attached to a horizontal, rotating plate 575 with brackets 580 such that the source/detector combination can rotate around the sample 530, through the requisite phi angles, but without interfering with the tape's linear movement path in and out of the measurement area. The sample may move continuously through the measurement zone using known actuation principles, or can be fixed during measurement. Notably in this example, plate 585 is approximately U-shaped, and fixedly suspends the source/detector combination over the sample 530, and is tilted (somewhat wrapped) around the post to provide a coordinated, symmetric beam movement through the requisite phi angles. Tilting can also be used to achieve the requisite chi (tilt) angle of about 55 degrees in one embodiment. This movement can be accomplished manually, or using a controllable motor.

The entire assembly can be supported by a base structure 560.

While the source and detector are shown directly opposed on axis "A" (FIG. 1), they only need to be in some fixed relationship during rotation, not necessarily opposing.

Dynamically Changing Samples:

Common to all of the above-discussed systems are samples that dynamically change based on, e.g., movement relative to the detector. In the fluid example (e.g., FIG. 3), the sample may be a fluid (diesel fuel) flowing through a pipeline, and requiring analysis of the amount of sulfur in the fuel. In the sheet examples (e.g., FIGS. 4–5), the sample may be sheet-like material such as steel requiring a phase measurement, or superconducting tape requiring a texture measurement. As used herein, the term "dynamically changing" is broadly construed to include both real time movement of the sample past the detector, as well as a general movement of a material through a measurement system, but with potential "snapshot" measurements of sample areas of the material in a static state. In either case, the measurement results are expected to vary over time given the changes in the composition of the sample from measurement-to-measurement.

When such measurement-to-measurement changes are expected, it is important to distinguish between significant and insignificant changes. The present system, in one embodiment, is a method and system for distinguishing between significant and insignificant changes in measurements, and adjusting the measurement system's outputs to a user accordingly.

Figure 6:
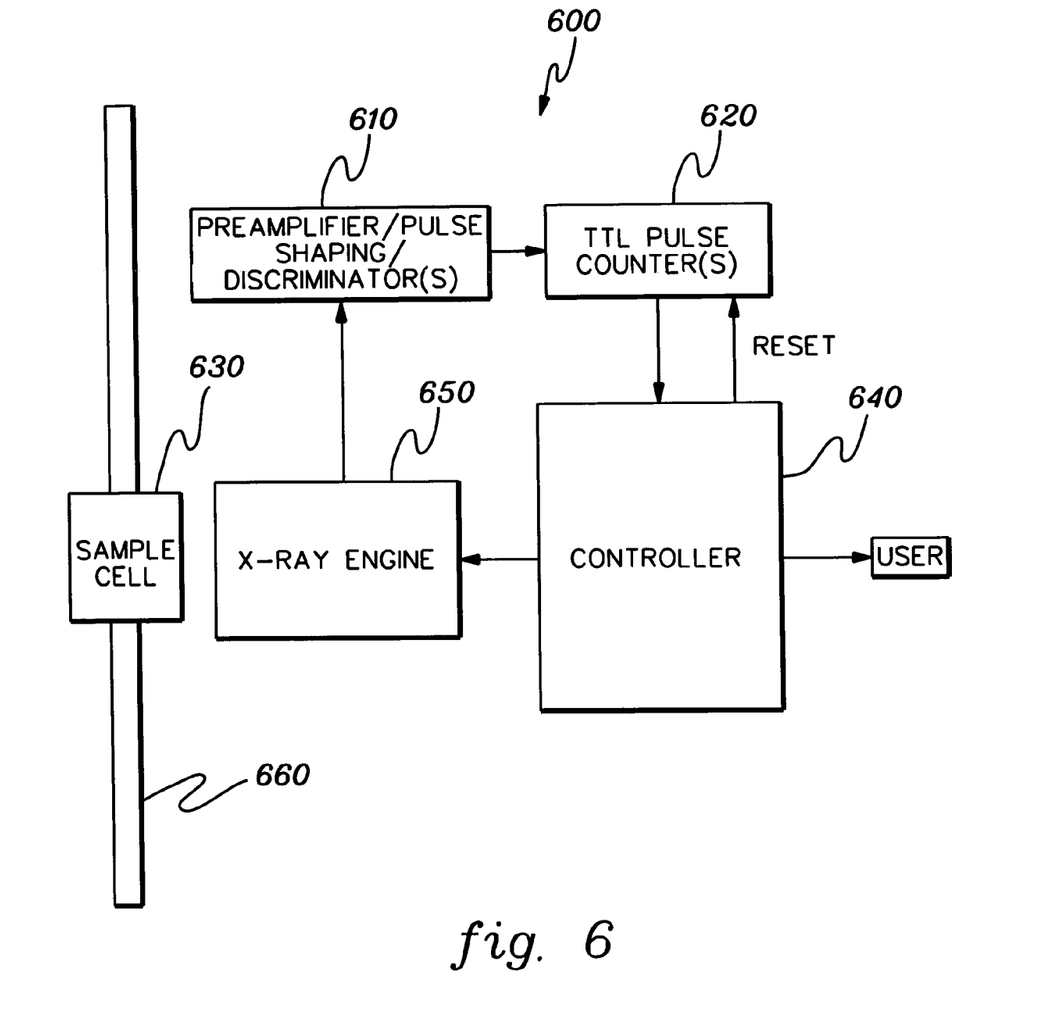
FIG. 6 is a flow diagram of an exemplary measurement processing system for x-ray data obtained from the exemplary x-ray engines of FIGS. 1–5.

FIG. 6 is an exemplary measurement processing system 600 which can be used in connection with any of the above x-ray engines. System 600 includes the engine 650, a sample cell 630, and a sample movement mechanism 660 (i.e., fluid pipeline, steel sheet production line, etc.). X-ray engine 650 usually produces an analog signal representative of an arrival of a photon of interest at the detector (not shown here for clarity). As discussed above, in monochromatic systems, the range of expected photon energies can be tailored to the analyte of interest (e.g., sulfur). The analog signal may be proportional to the photon's energy, and can pre-processed by a bank of circuitry 610. This circuitry can include pre-amplifiers, pulse shapers, and discriminator(s) to further filter the engine's analog output into a digital pulse stream (e.g., TTL), each pulse related to the arrival of a photon at an energy of interest. A single discriminator channel can be used to monitor a specific energy of interest, or multiple discriminator channels can be used to monitor multiple energies of interest, each producing a respective data stream.

A bank of resettable TTL counter(s) 620 can be used to count the number of pulses as they arrive from a respective discriminator.

Controller 640 can periodically "sample" the output register of the counters, and reset the counters at some desired frequency, or pulse integration period.

Thus, the values sampled from the counters 620 by the controller 640 are related to the number of photons received at the relevant energies of interest, and thus the compositional makeup of the sample. These counts, however, are subject to change along with the dynamically changing nature of the sample.

Figure 7A:
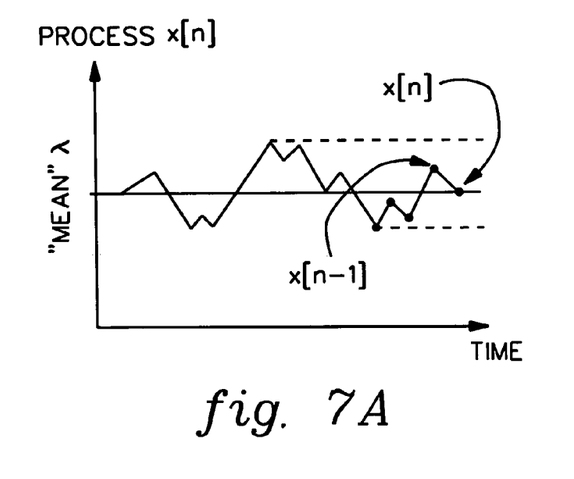
FIGS. 7a–c are diagrams depicting the Poisson distribution which is approximated according to the principles of the present invention.

The counts sampled by controller 640 can be considered as a stream of input values x[n], x[n−1], x[n−2] ... sampled at a sample period T in accordance with the principles of the present invention, as shown in FIG. 7a. The probability P that the current input value x[n] is within the two sided region +/−Δx of the prior input value x[n−1] can be estimated with the Poisson arrival distribution as follows:

$$P(x[n]) = \int_{x=x[n-1]-\Delta x}^{x=x[n-1]+\Delta x} \frac{x[n-1]^x e^{-x[n-1]}}{x!} dx \quad (1)$$

Figure 7B:
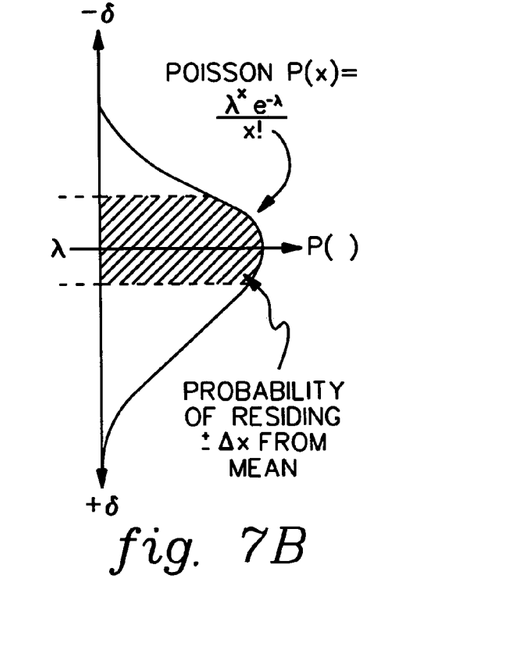
Figure 7C:
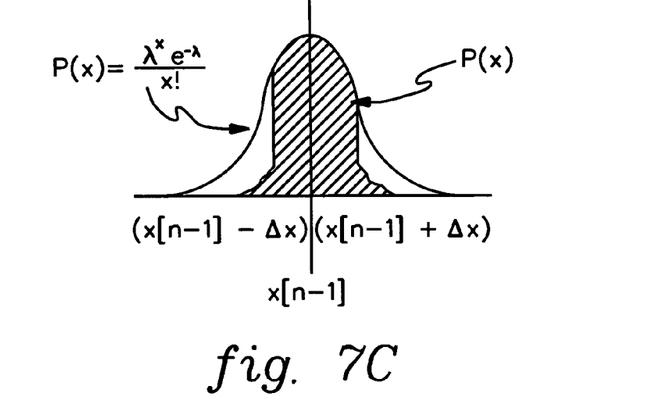

Equation (1) is simply an expression that calculates the probability of the current input x[n] being some distance from the prior input x[n−1]. As such, the likelihood that x[n] is identical to x[n−1] is very small because Δx is small; the probability that x[n] is within all Δx of x[n−1] is 1.0 since all probability is integrated. The expression 1−P(x[n]) is then the probability that the change between x[n] and x[n−1] is insignificant. When x[n] and x[n−1] are similar values the probability that the change between x[n] and x[n−1] is insignificant is large. Conversely, when x[n] and x[n−1] differ by a large amount, the probability that this difference is insignificant is small. (See, e.g., FIGS. 7b–7c.) An exemplary approximation to (1) is a linear difference based on the number of standard deviations that Δx must assume before the variable d assumes a unit value, where the standard deviation of the example Poisson distribution is $\sqrt{x[n-1]}$:

$$d = \frac{|x[n] - x[n-1]|}{S\sqrt{x[n-1]}} \quad (2)$$

In this relation, the value S is programmable, and is chosen as the number of standard deviations the user considers to be "significant."

A low pass, single pole filter of the following form can be used, with coefficient p and representing a moving pole:

$$y[n] = (1-p)x[n] + py[n-1] \quad (3)$$

Figure 8:
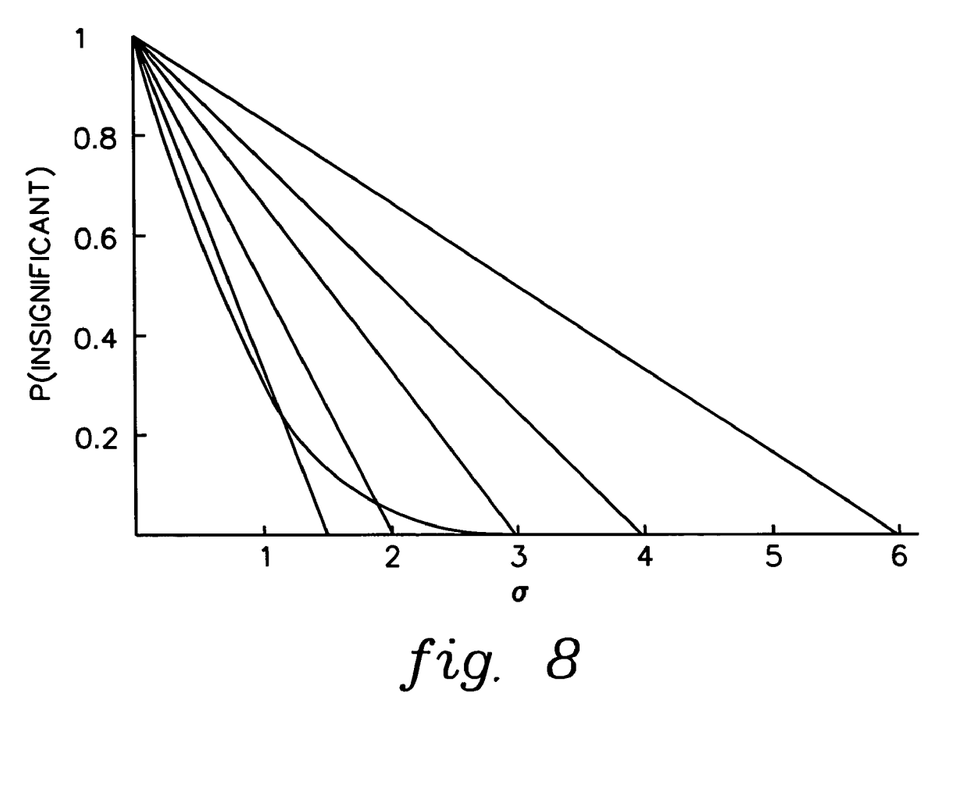
FIG. 8 is a graph serving as the basis of the linear approximation of the distribution in accordance with the present invention.

The value p, though a continuous function of d in (2), can be clamped between 1 and a small (or 0) constant δ associated with implementation precision, to define the filter pole in the unit circle, and normalize the probability function. Equation (4) linearly approximates 1−P(x[n]) based on choice of programmable value S as shown in FIG. 8:

$$p = 1 - \min\left(1, \max\left(\frac{|x[n] - x[n-1]|}{S\sqrt{x[n-1]}}, \delta\right)\right) \quad (4)$$

If p~a small (or 0) constant δ (changes are significant):

$$y[n] = (1-p)x[n] + py[n-1] = (1-0)x[n] + 0y[n-1] = x[n] \quad (5)$$

In (5) the output value y[n] is "forced" to the last input value x[n], because this value is deemed a significant change in measured compositional input value.

And as p approaches 1 (changes are insignificant):

$$y[n] = (1-p)x[n] + py[n-1] = (1-1)x[n] + 1y[n-1] = y[n-1] \quad (6)$$

In (6), the output value y[n] is simply "forced" to the last output value y[n−1] because the input compositional value x[n] has not changed significantly from the previous input compositional value x[n−1].

The present invention therefore uses the value "p" as a coefficient in the low-pass filter implementation (3). This value is maintained in (2) and (4) as a function of the intensity of the input values themselves, x. Thus the deviation limit upon which the input values are tested is continuously updated as a function of the input values themselves. This adaptive maintenance of the deviation limit allows the x-ray engines to use the intrinsic properties of the Poisson distribution to advantage. This advantage is prior knowledge of the distribution of the random variables x[n] and x[n−1], as well as the increase in precision associated with the value of random variable x[n] as the magnitude of the random variable x[n] increases.

Figure 9:
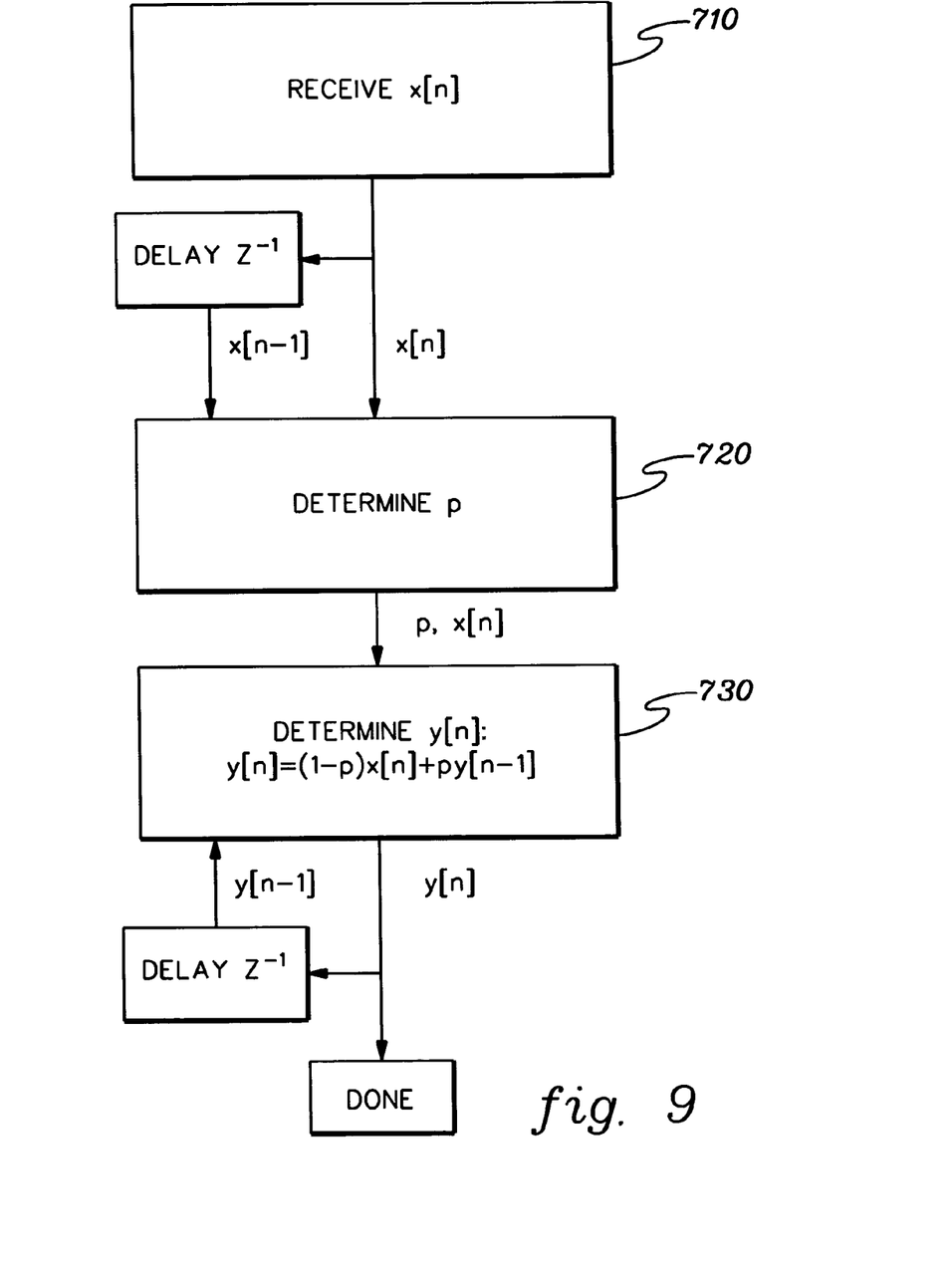
FIG. 9 is a flow diagram depicting one exemplary processing technique in accordance with the principles of the present invention.

The exemplary flow diagram of FIG. 9 depicts one embodiment of the processing of the present invention, which can be implemented in the automated controller 640 in FIG. 6 as any combination of hardware and software. The current measurement value x[n] is received 710, and with its previous, delayed value x[n−1] are used in the calculation of p in 720, in accordance with (2) and (4) above. The low pass filter implementation is implemented in 730, with the output y[n] sent to the user (FIG. 6) and also delayed for the calculation of the "next" y[n].

Initial conditions can be set according to expected values, depending on the measurement at hand, and any intentional changes in the sample and/or sample measurement technique, or other changes in the system.

The present invention is not limited to any particular detection mechanism—as discussed above some energy resolution can be effected at the detector, and/or in downstream discriminators. The present invention is applicable to any type of measurement system in which dynamically changing samples are of interest, including any of the XRF and XRD systems discussed above.

Also, the present invention as disclosed above is directed to a single sample memory x[n−1], and a single pole filter, but those skilled in the art will recognize that the principles herein are extendable to the use of multiple past signal samples, as well as multiple-pole and multiple tap filters. Moreover, the value p can also be maintained as a function of past y values, as well as a function of past x values as discussed above.

The present invention can be included in an article of manufacture (e.g., one or more computer program products) having, for instance, computer usable media. The media has embodied therein, for instance, computer readable program code means for providing and facilitating the capabilities of the present invention. The article of manufacture can be included as a part of a computer system or sold separately.

Additionally, at least one program storage device readable by a machine, tangibly embodying at least one program of instructions executable by the machine to perform the capabilities of the present invention can be provided.

The flow diagrams depicted herein are just exemplary. There may be many variations to these diagrams or the steps (or operations) described therein without departing from the spirit of the invention. For instance, the steps may be performed in a differing order, or steps may be added, deleted or modified. All of these variations are considered a part of the claimed invention.

Further, the objects, operands and controls described herein are only exemplary. Additional or differing objects, operands and/or controls may be used in other embodiments.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the following claims.

What is claimed is:

1. A method for suppressing statistically insignificant variations in data representing measured compositional information from a dynamically changing sample in an automated analysis system, comprising:
   measuring the compositional information using an analysis technique, including
      stimulating the sample, and
      detecting emissions emitted from the sample;
   receiving a stream of input values x[n], x[n−1], x[n−2] . . . related to the measured compositional information of the sample;
   determining a stream of output values y[n], y[n−1], y[n−2] . . . related to said compositional information, including:
      setting the output y[n] as a function of the received input value x[n] if the received input value x[n] differs from x[n−1] by more than an intensity-dependent deviation limit, and
      setting the output y[n] as a function of the previous output y[n−1] and the received input value x[n] if the received input value x[n] differs from x[n−1] by less than the intensity-dependent deviation limit,
   wherein the intensity-dependent deviation limit is maintained as a function of the input values; and
   presenting measurement results related to the output y[n] to a user via a controller.

2. The method of claim 1, wherein said determining comprises:
   maintaining the intensity-dependent deviation limit as a function of:

$$\frac{|x[n] - x[n-1]|}{S\sqrt{x[n-1]}}$$

where S is a predetermined value controlling the deviation limit.

3. The method of claim 2, wherein said determining comprises:
   maintaining the deviation limit according to the following function:

$$p = 1 - \min\left(1, \max\left(\frac{|x[n] - x[n-1]|}{S\sqrt{x[n-1]}}, \delta\right)\right)$$

and wherein if p~a small (or 0) constant δ, then x[n] differs from x[n−1] by the deviation limit; and wherein if p~1, then x[n] differs from x[n−1] by less than the deviation limit.

4. The method of claim 3, wherein y[n] is determined as follows:

$$y[n]=(1-p)x[n]+py[n-1].$$

5. The method of claim 1, wherein said measuring includes:
   measuring the compositional information using an x-ray analysis technique, including
      using a source for directing excitation x-ray, neutron, particle-beam or gamma ray radiation toward a sample;
      using a detector for detecting emissions emitted from the sample.

6. The method of claim 5, wherein the sample is a fluid or solid, substantially moving relative to the source and/or detector.

7. The method of claim 6, wherein said measuring includes using an x-ray fluorescence or diffraction technique.

8. The method of claim 5, wherein said measuring includes using an x-ray fluorescence or diffraction technique.

9. The method of claim 1, wherein the sample is a fluid or solid, substantially moving relative to a source and/or detector used to measure said compositional information.

10. A system for suppressing statistically insignificant variations in data representing measured compositional information from a dynamically changing sample in an automated analysis system, comprising:
   means for measuring the compositional information using an analysis technique, including
      means for stimulating the sample, and
      means for detecting emissions emitted from the sample;
   means for receiving a stream of input values x[n], x[n−1], x[n−2] . . . related to measured compositional information of the sample;
   means for determining a stream of output values y[n], y[n−1], y[n−2] . . . related to said compositional information, including:
      means for setting the output y[n] as a function of the received input value x[n] if the received input value x[n] differs from x[n−1] by more than an intensity-dependent deviation limit, and means for setting the output y[n] as a function of the previous output y[n−1] and the received input value x[n] if the received input value x[n] differs from x[n−1] by less than the intensity-dependent deviation limit, wherein the intensity-dependent deviation limit is maintained as a function of the input values; and controller means for presenting measurement results related to the output y[n] to a user.

11. The system of claim 10, wherein said means for determining comprises:

means for maintaining the intensity-dependent deviation limit as a function of:

$$\frac{|x[n]-x[n-1]|}{S\sqrt{x[n-1]}}$$

where S is a predetermined value controlling the deviation limit.

12. The system of claim 11, wherein said means for determining comprises:

means for maintaining the deviation limit according to the following function:

$$p = 1 - \min\left(1, \max\left(\frac{|x[n]-x[n-1]|}{S\sqrt{x[n-1]}}, \delta\right)\right)$$

and wherein if p~a small (or 0) constant δ, then x[n] differs from x[n−1] by the deviation limit; and wherein if p~1, then x[n] differs from x[n−1] by less than the deviation limit.

13. The system of claim 12, wherein y[n] is determined as follows:

$y[n]=(1-p)x[n]+py[n-1]$.

14. The system of claim 10, in combination with an x-ray engine measuring the compositional information using an x-ray analysis technique, wherein:

the means for stimulating comprises a source for directing excitation x-ray, neutron, particle-beam or gamma ray radiation toward a sample;

the means for detecting comprises a detector for detecting emissions emitted from the sample.

15. The combination of claim 14, wherein the sample is a fluid or solid, substantially moving relative to the source and/or detector.

16. The combination of claim 15, wherein said x-ray engine uses an x-ray fluorescence or diffraction technique.

17. The combination of claim 14, wherein said x-ray engine uses an x-ray fluorescence or diffraction technique.

18. The system of claim 10, wherein the sample is a fluid or solid, substantially moving relative to a source and/or detector used to measure said compositional information.

19. A program storage device readable by a machine, tangibly embodying at least one program of instructions executable by the machine for suppressing statistically insignificant variations in data representing measured compositional information from a dynamically changing sample in an automated analysis system which measures the compositional information using an analysis technique which includes stimulating the sample and detecting emissions emitted from the sample, comprising:

program code means for receiving a stream of input values x[n], x[n−1], x[n−2] . . . related to measured compositional information of the sample;

program code means for determining a stream of output values y[n], y[n−1], y[n−2] . . . related to said compositional information, including:

program code means for setting the output y[n] as a function of the received input value x[n] if the received input value x[n] differs from x[n−1] by more than an intensity-dependent deviation limit, and program code means for setting the output y[n] as a function of the previous output y[n−1] and the received input value x[n] if the received input value x[n] differs from x[n−1] by less than the intensity-dependent deviation limit, wherein the intensity-dependent deviation limit is maintained as a function of the input values; and program code means for presenting measurement results related to the output y[n] to a user via a controller.

20. The device of claim 19, wherein said program code means for determining comprises:

program code means for maintaining the intensity-dependent deviation limit as a function of:

$$\frac{|x[n]-x[n-1]|}{S\sqrt{x[n-1]}}$$

where S is a predetermined value controlling the deviation limit.

21. The device of claim 20, wherein said program code means for determining comprises:

program code means for maintaining the deviation limit according to the following function:

$$p = 1 - \min\left(1, \max\left(\frac{|x[n]-x[n-1]|}{S\sqrt{x[n-1]}}, \delta\right)\right)$$

and wherein if p~a small (or 0) constant δ, then x[n] differs from x[n−1] by the deviation limit; and wherein if p~1, then x[n] differs from x[n−1] by less than the deviation limit.

22. The device of claim 21, wherein y[n] is determined as follows:

$y[n]=(1-p)x[n]+py[n-1]$.

23. The device of claim 19, in combination with an x-ray engine measuring the compositional information using an x-ray analysis technique, the x-ray engine including:

a source for directing excitation x-ray, neutron, particle-beam or gamma ray radiation toward a sample;

a detector for detecting emissions emitted from the sample.

24. The combination of claim 23, wherein the sample is a fluid or solid, substantially moving relative to the source and/or detector.

25. The combination of claim 24, wherein said x-ray engine uses an x-ray fluorescence or diffraction technique.

26. The combination of claim 23, wherein said x-ray engine uses an x-ray fluorescence or diffraction technique.

27. The device of claim 19, wherein the sample is a fluid or solid, substantially moving relative to a source and/or detector used to measure said compositional information.

* * * * *